(12) United States Patent
Kudo et al.

(10) Patent No.: US 6,803,465 B2
(45) Date of Patent: Oct. 12, 2004

(54) OPTICALLY ACTIVE 4-(TERT-BUTOXYCARBONYL)PIPERAZINE COMPOUND, AND METHOD FOR PRODUCING THE SAME

(75) Inventors: Junko Kudo, Ibaraki (JP); Norihiko Hirata, Suita (JP); Tomoyasu Yoshida, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/076,448

(22) Filed: Feb. 19, 2002

(65) Prior Publication Data

US 2002/0128275 A1 Sep. 12, 2002

(30) Foreign Application Priority Data

Feb. 22, 2001 (JP) ......................................... 2001-046390

(51) Int. Cl.⁷ ................. C07D 295/185; C07D 295/073
(52) U.S. Cl. ......................................... 544/389; 544/396
(58) Field of Search ................................. 544/389, 396

(56) References Cited

U.S. PATENT DOCUMENTS

| | | | |
|---|---|---|---|
| 2,819,269 A | * | 1/1958 | Weston et al. |
| 5,478,941 A | | 12/1995 | Cossement et al. |
| 5,703,082 A | | 12/1997 | Cossement et al. |
| 5,792,770 A | | 8/1998 | Cossement et al. |

FOREIGN PATENT DOCUMENTS

| | | |
|---|---|---|
| GB | 2 225 321 A | 5/1990 |
| JP | 7-2816 A | 1/1995 |

OTHER PUBLICATIONS

Plobeck et al., J.Med.Chem. vol. 43,p. 3878–3894 (2000).*
C.J. Opalka et al., "A Novel Synthesis of the Enantiomers of an Antihistamine Drug by Piperazine Formation from a Primary Amine", Synthesis, (1995), pp. 766–768.
G.R. Clemo et al., "The Optical Rotatory Powers of Some 4-Substituted Benzhydrylamines", J. Chem. Soc., (1939), pp. 1958–1960.

\* cited by examiner

*Primary Examiner*—Emily Bernhardt

(57) ABSTRACT

A method for producing 1-[(substituted phenyl) phenylmethyl]piperazines useful as intermediates for pharmaceuticals and the like, more particularly, for example, to an intermediate for the production of antiallergic pharmaceuticals. A 4-(tert-butoxycarbonyl)piperazine compound of formula (1):

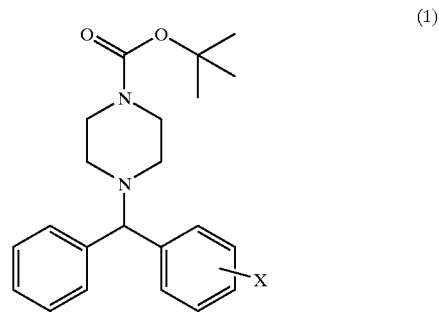

(1)

wherein X denotes a chlorine atom, a C1–C3 alkyl group or a C1–C3 alkoxy group, and an optical isomer present therein.

17 Claims, No Drawings

OPTICALLY ACTIVE 4-(TERT-BUTOXYCARBONYL)PIPERAZINE COMPOUND, AND METHOD FOR PRODUCING THE SAME

FIELD OF THE INVENTION

The present invention relates to a method for producing 1-[(substituted phenyl)phenylmethyl]piperazine, which is useful as intermediates for pharmaceuticals and the like, more particularly, for example, to an intermediate for the production of antiallergic pharmaceuticals disclosed in JP-A-7-2816.

BACKGROUND OF THE INVENTION

An optical resolution method of an optically active 1-[(substituted phenyl)phenylmethyl]piperazine is disclosed in GB 2225321, which method comprises reacting racemic 1-[(4-chlorophenyl)phenylmethyl]piperazine with an optically active tartaric acid to form a salt.

JP-A-7-2816 discloses a method comprising the steps of performing optical resolution by allowing racemic (4-chlorophenyl)phenylmethylamine to react with optically active tartaric acid to form a salt, reacting the salt with N,N-bis(2-chloroethyl)-4-methylbenzenesulfonamide to form 1-[(4-chlorophenyl)phenylmethyl]-4-[(4-methylphenyl)sulfonyl]-piperazine, and removing the 4-methylbenzenesulfonyl group from the 1-[(4-chlorophenyl)phenylmethyl]-4-[(4-methylphenyl)sulfonyl]-piperazine to produce 1-[(4-chlorophenyl)phenylmethyl] piperazine.

The former method has a problem in that the optical resolution yield is as low as 13%. The latter method has a problem in that the method needs a plurality of expensive reagents and is tedious.

SUMMARY OF THE INVENTION

According to the present invention, optically active 1-[(4-chlorophenyl)phenylmethyl]piperazine can be efficiently produced in a good yield, by using industrially readily available compounds.

The present invention provides:

1. a composition comprising
an optical isomer of formula (1"):

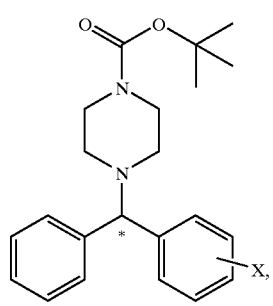

(1")

wherein X denotes a chlorine atom, a C1–C3 alkyl group or a C1–C3 alkoxy group and * designate an asymmetric carbon atom, and
an enantiomer thereof, in an optional ratio;

2. a process for producing a racemic 4-(tert-butoxycarbonyl)piperazine compound of formula (1):

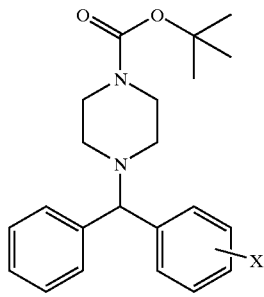

(1)

wherein X denotes a chlorine atom, a C1–C3 alkyl group or a C1–C3 alkoxy group, which comprises reacting 1-[(substituted phenyl) phenylmethyl]piperazin of formula (4):

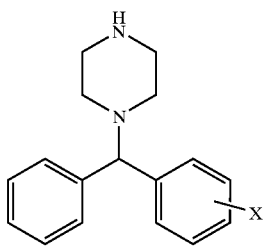

(4)

wherein X has the same meaning as defined above, with di-tert-butyl dicarbonate of formula (5):

$$[(CH_3)_3COCO]_2O \quad (5);$$

3. an adduct salt of formula (3):

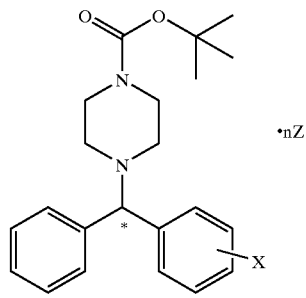

(3)

wherein X denotes a chlorine atom, a C1–C3 alkyl group or a C1–C3 alkoxy group and * designate an asymmetric carbon atom, n represents an integer of 1 or 2, and Z represents
an optically active acid of formula (2):

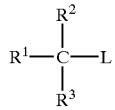

(2)

wherein L represents —COOH or —SO$_3$H,
R$^2$ represents a hydrogen atom or a hydroxyl group,
R$^1$ and R$^3$ are the same or different and each independently represent
a hydrogen atom, a halogen atom, an arylcarbonyloxy group, a liner or branched alkyl group which may be substituted with at least one group selected from a hydroxyl group, a halogen atom, arylcarbonyloxy, carboxy and arylaminocarbonyl;

an aryl group which may be substituted with at least one group selected from a halogen atom, alkyl and alkoxy;

an aralkyl group which may be substituted with at least one group selected from a halogen atom, alkyl, alkoxy and a hydroxyl group;

an aryloxy group which may be substituted with at least one group selected from a halogen atom, alkyl, alkoxy and a hydroxyl group;

a cyclic alkyloxy group which may be substituted with at least one group selected from a halogen atom, alkyl, alkoxy or a hydroxyl group; or a cyclic alkyl group which may be substituted with at least one group selected from a halogen atom, alkyl, alkoxy, a hydroxyl group and a phenylcarbonylamino group; or $R^1$ and $R^3$ may be bonded together to form an alkylene group which may be substituted with at least one group selected from a halogen atom, an alkyl alkoxy, carboxyl, oxo, hydroxyl, and a phenylcarbonylamino group; or a heterocycle which may be substituted with at least one group selected rom an alkyl group, alkoxy or a halogen atom;

4. a process for producing the adduct salt of formula (3) as defined above, which comprises reacting a composition comprising an optical isomer of 4-(tert-butoxycarbonyl)piperazine compound of formula (1") as defined above and an enantiomer thereof, with an optically active acid of formula (2) as defined above;

5. a process for producing an adduct salt of formula (6):

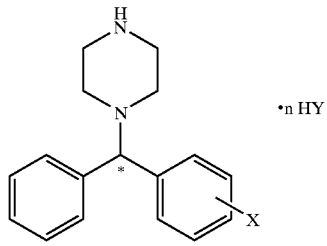

(6)

wherein X denotes a chlorine atom, a C1–C3 alkyl group or a C1–C3 alkoxy group, * represents an asymmetric carbon atom, and n represents an integer of 1 or 2, Y represents a halogen atom, —OSO₃H, —OSO₂CH₃, —OCOCF₃, —OCOCH₃ and —OCOH, which comprises reacting an optically active 4-(tert-butoxycarbonyl) piperazine of formula (1') as defined above with an acid of formula: HY, wherein Y represents the same as defined above; and 6. a process for producing an optically active 1-[(substituted phenyl)phenylmethyl]piperazine of formula (7):

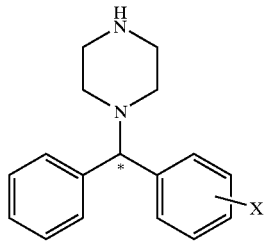

(7)

wherein X and * each have the same meaning as defined above, which process comprises reacting an optically active 4-(tert-butoxycarbonyl)piperazine compound of formula (1') as defined above, with an acid, and optionally subsequently with a base.

DETAILED DESCRIPTION OF THE INVENTION

Hereinafter, the present invention will be described in detail.

First a description will be made to the composition (hereinafter referred to as "the present composition") comprising an optical isomer of formula (1") as defined above and an enantiomer thereof in an optional ratio.

The present composition encompasses:

(a) a racemic 4-(tert-butoxycarbonyl)piperazine compound of formula (1) as defined above;

(b) an optically active 4-(tert-butoxycarbonyl)piperazine compound of formula (1'):

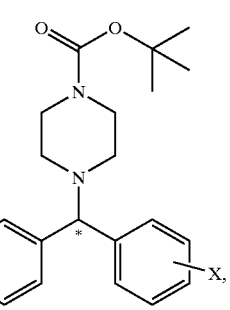

(1')

wherein X denotes a chlorine atom, a C1–C3 alkyl group or a C1–C3 alkoxy group and * designate an asymmetric carbon atom;

(c) a composition comprising an optical isomer of 4-(tert-butoxycarbonyl)piperazine compound of formula (1") as defined above and an enantiomer thereof, which composition encompasses (a), wherein the optical isomer and an enantiomer thereof are present in equal amount, and (b), wherein one optical isomer is present in excess to the enatiomer thereof, and (d) an optical isomer of formula (1") as defined above.

In the formula (1), (1') and (1"), examples of the C1–C3 alkyl group include methyl, ethyl, n-propyl, and i-propyl groups, and examples of the C1–C3 alkoxy group include methoxy, ethoxy, n-propoxy, and i-propoxy groups.

Next a description will be made to the 4-(tert-butoxycarbonyl)piperazine compound of formula (1) of the present invention. The compound of formula (1) can be produced by a process which comprises reacting the 1-[(substituted phenyl)phenylmethyl]piperazine of formula (4) with di-tert-butyl dicarbonate in the presence of a base.

The amount of the di-tert-butyl dicarbonate to be used is preferably from 0.5 to 10 moles, more preferably approximately from 1 to 5 moles per mol of the 1-[(substituted phenyl)phenylmethyl]piperazine of formula (4).

Examples of the base include, for example, an inorganic base such as an alkali metal hydroxide such as sodium hydroxide, potassium hydroxide, or the like, an alkaline earth metal hydroxide such as barium hydroxide, calcium hydroxide, or the like, an alkali metal carbonate such as sodium carbonate, potassium carbonate, or the like, an alkali metal hydrogencarbonate such as sodium hydrogencarbonate, potassium hydrogencarbonate or the like; and an organic base such as triethylamine, N,N-diisopropylethylamine, N,N,N',N'-tetramethylethylenediamine, N-methylpiperazine, N-methyl morpholine, N-methylimidazole, pyridine, 4-dimethylaminopyridine or a mixture thereof The base is preferably used in an amount of from 0.01 to 10 moles, more preferably approximately from 0.1 to 5 moles per mol of the di-tert-butyl dicarbonate.

The reaction is usually performed in a solvent. Examples of the solvent include, for example, an aromatic hydrocarbon such as toluene, benzene, xylene, or the like, an aliphatic hydrocarbon such as hexane, heptane, or the like, a halogenated hydrocarbon such as dichloromethane, dichloroethane, chloroform, 1-chlorobutane, chlorobenzene, or the like, an ether such as diethyl ether, tert-butyl methyl ether, tetrahydrofuran, dimethoxyethane, diglyme, triglyme, or the like, a ketone such as acetone, methyl ethyl ketone, methyl isobutyl ketone, or the like, an amide such as N,N-dimethylformamide, N,N-dimethylacetamide, or the like, an alcohol such as 1-propanol, 2-propanol, tert-butanol, or the like, a nitrile such as acetonitrile or the like, and water, or a mixture thereof. Any suitable amount of the solvent may be used, and it is preferably used in an amount of from 0.5 to 100 parts by weight, preferably from 1 to 30 parts by weight per 1 part by weight of the 1-[(substituted phenyl)phenylmethlyl]piperazine of formula (4).

The reaction is usually conducted by mixing 1-[(substituted phenyl)phenylmethyl]piperazine of formula (4), di-tert-butyl dicarbonate and a base in a solvent.

The reaction temperature ranges usually from −50 to 100° C., preferably approximately from 0 to 50° C.

After completion of the reaction, the obtained 4-(tert-butoxycarbonyl)piperazine compound of formula (1) can be used in a solution form as it is for the following reaction. However, the product may be isolated, for example, by using water and a water-immiscible organic solvent (e.g, the aliphatic, aromatic or halogenated hydrocarbon solvent, ether, t-butyl methyl ether, methyl isobutyl ketone, or the like) followed by phase separation, thereby removing the base that may be present in the organic layer, and removing the solvent by distillation. The product may also be isolated by crystallization by cooling in a solvent, followed by filtration.

The racemic 1-[(substituted phenyl)phenylmethyl] piperazine compound of formula (4):

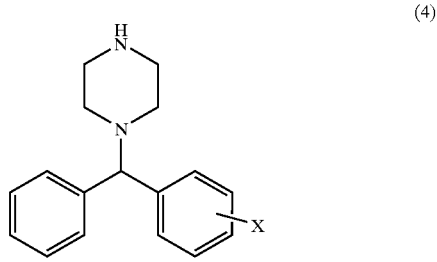

(4)

wherein X has the same meaning as defined above can be produced, for example, according to a method described in JP4-154736A or a method described in JP61-35189B, The optically active 4-(tert-butoxycarbonyl)piperazine compound of formula (1') can be produced by a process which comprises reacting the racemic 4-(tert-butoxycarbonyl)piperazine compound of formula (1) with the optically active add of formula (2) as defined above to produce an optically active adduct salt of formula (3), and reacting the salt (3) with a base.

A description will be made to the $R^1$ to $R^3$ in the optically active acid of formula (2) as defined above.

Examples of the halogen atom represented by $R^1$ or $R^3$ group or that may be present therein in the present specification include fluorine, chlorine, bromine, and iodine.

Examples of the "aryl" in the aryl, aryloxy, arylcarbonyloxy, arylcarbonyloxy, arylaminocarbonyl, and aralkyl groups in $R^1$ or $R^3$ include, for example, a phenyl or naphthyl group or the like.

Examples of the linear or branched alkyl group include, for example, a linear or branched (C1–C6)alkyl group such as methyl, ethyl, n-propyl, i-propyl, n-butyl, s-butyl, t-butyl, i-butyl, n-pentyl, t-pentyl, neo-pentyl, s-pentyl, i-pentyl group, or n-hexyl group, or the like, Examples of the linear or branched alkoxy group include, for example, a linear or branched (C1–C6)alkoxy group such as methoxy, ethoxy, n-propoxy, i-propoxy, n-butoxy, s-butoxy, t-butoxy, i-butoxy, n-pentyloxy, t-pentyloxy, neo-pentyloxy, s-pentyloxy, i-pentyloxy group, or n-hexyloxy group or the like.

Examples of the aralkyl group include, for example, a (C7–C12)aralkyl group such as a benzyl group, a phenethyl group, a naphthylmethyl group, a naphthylethyl group or the like.

Examples of the cycloallyloxy group include, for example, a (C5–C10)cycloalkyloxy group such as a cyclopentyloxy group, cyclohexyloxy group, a meathyloxy group or the like.

Examples of the cycloalkyl group include, for example, a (C5–C7)cycloalkyl group such as a cyclopentyl group, a cyclohexyl group, a norcamphanyl(bicyclo[2.2.1]heptyl group) group or the like.

Examples of the alkylene group that may be formed from $R^1$ and $R^3$ include, for example, a (C4–C5)alkylene group such as tetramethylene, pentamethylene group or the like.

Examples of the heterocycle include, for example, a tetrahydrofuranyl group and the like.

Examples of the alkyl group in the alkyl or alkoxy group that may be present on the aryl, aryloxy; aralkyl, cycloalkyloxy, cycloalkyl, alkylene or the heterocycle include, for example, a (C1–C3)alkyl group such as a methyl group, an ethyl group, a n-propyl group, or an i-propyl group.

Specific examples of the alkoxy group that may be present on the aryl, aryloxy, aralkyl, cycloalkyloxy, cycloalkyl, alkylene or the heterocycle include, for example, a methoxy group, an ethoxy group, and an n-propoxy group.

With respect to the optically active acid of formula (2), $R^1$ to $R^3$ and L groups may represent different groups and the carbon atom bonded with the four groups may be an asymmetric carbon atom, alternatively, $R^1$ or $R^3$ may be an optically active group.

Specific examples of the acid of formula (2) include, for example, L-tartaric acid, L-O,O'-dibenzoyltartaric acid, (S)-2-chloropropionic acid, (S)-2-phenylpropionic acid, (S)-2-phenoxypropionic acid, (S)-2-(6-methoxy-2-naphthyl) propionic acid, (S)-2,3-diphenylpropionic acid, L-mandelic acid, (S)-3-chloromandelic acid, L-lactic acid, L-malic acid, (2R, 3R)-tartranilic acid, (S)-2-(4-chlorophenyl)isovaleric acid, (1R, 3R, 4R, R5)-quinic acid, (S)-2-benzylsuccinic acid, (S)-tetrahydro-2-furancarboxylic acid, (1R, 2S)-2-benzamidecyclohexanecarboxylic acid, (1R, 2R, 5R)-menthoxyacetic acid, (1R, 3S)-camphoric acid, (1R)-10-camphorsulfonic acid, (1R)-3-bromocamphor-8-sulfonic acid and optical isomers thereof.

The optically active acid is allowed to react with an enantiomer of the 4-(tert-butoxycarbonyl)piperazine compound of formula (1") to precipitate preferentially a formed diastereomer salt of the optically active acid, which can be then separated by an appropriate manner.

The optically active acid is usually used in an amount of from 0.1 to 10 moles, preferably approximately from 0.3 to 3 moles per mol of the 4-(tert-butoxycarbonyl)piperazine compound of formula (1).

The reaction is usually performed in a solvent. Examples of the solvent include, for example, the same solvent as described. Any suitable amount of the solvent may be used and it is usually from 0.5 to 100 parts by weight, preferably from 1 to 30 parts by weight per 1 part by weight of the 4-(tert-butoxycarbonyl)piperazine of formula (1).

The reaction is typically performed by mixing the 4-(tert-butoxycarbonyl)piperazine compound of formula (1) and the acid of formula (2) in a solvent. The reaction temperature ranges usually from −50 to 100° C., preferably approximately from 0 to 50° C.

After completion of the reaction, the obtained optically active adduct salt of the optically active 4-(tert-butoxycarbonyl)piperazine compound of formula (3) can be isolated by a conventional method, for example, by filtration.

In the filtrate, there may exist the antipode of the 4-(tert-butoxycarbonyl)piperazine compound of formula (1) as the salt with the optically active acid after the filtration, and the antipode may be isolated, for example, by distilling the solvent.

Examples of the optically active adduct salt of the optically active 4-(tert-butoxycarbonyl)piperazine compound of formula (3) include, for example, a mono or di-adduct salt of L-tartaric acid, L-O,O'-dibenzoyltartaric acid, (S)-2-chloropropionic acid, (S)-2-phenylpropionic acid, (S)-2-phenoxypropionic acid, (S)-2-(6-methoxy-2-naphthyl) propionic acid, (S)-2,3-diphenylpropionic acid, L-mandelic acid, (S)-3-chloromandelic acid, L-lactic acid, L-malic acid, (2R, 3R)-tartranilic acid, (S)-2-(4-chlorophenyl)isovaleric acid, (1R, 3R, 4R, R5)-quinic acid, (S)-2-benzylsuccinic acid, (S)-tetrahydo-2-furancarboxylic acid, (1R, 2S)-2-benzamidecyclohexanecarboxylic acid, (1R, 2R, 5R)-menthoxyacetic acid, (1R, 3S)-camphoric acid, (1R)-10-camphorsulfonic acid, (1R)-3-bromocamphor-8-sulfonic acid or a optical isomer thereof and 1-[(4-chlorophenyl)phenylmethyl]-4-(tert-butoxycarbonyl)piperazine.

Examples of the adduct salt further include, for example, an adduct salt having a chlorine atom at a position on the phenyl group other than 4-position, in place of the 4-chloro atom, in the 1-[(4-chlorophenyl)phenylmethyl]-4-(tert-butoxycarbonyl)piperazine of each salt described above, and an adduct salt having a C1–C3 alkyl group or a C1–C3 alkoxy group, in place of the 4-chloro atom, on the same or different position of the phenyl group of the 1-[(4-chlorophenyl)phenylmethyl]-4-(tert-butoxycarbonyl) piperazine in each salt described above.

These may contain optical isomers of 4-(tert-butoxycarbonyl)piperazine of formula (1") and the optically active acids in an arbitrary ratio.

Preferred is the salt of 1-[(4-chlorophenyl)phenylmethyl]-4-(tert-butoxycarbonyl)piperazine and optically active L-O, O'-dibenzoyltartaric acid.

The optical purity of the optically active adduct salt of the optically active 4-(tert-butoxycarbonyl)piperazine compound of formula (3) can be improved by recrystallization(s) in a solvent.

In the recrystallization, the optically active adduct salt of the optically active 4-(tert-butoxycarbonyl)piperazine compound of formula (3) having an improved optical purity can be isolated as crystals by cooling a solvent thereof, which may be prepared by dissolving it in a solvent.

The crystallization may be facilitated by adding a solvent (poor solvent) that shows insufficient solubility with respect to the optically active adduct salt of the optically active 4-(tert-butoxycarbonyl)piperazine compound of formula (3), to the reaction mixture or a solution containing the salts to be further purified.

The solvent that may be used to recrystalize the optically active adduct salt of 4-(tert-butoxycarbonyl)piperazine compound of formula (3) can be selected, for example, from a solvent as mentioned above depending on the salt to be crystallized. Any suitable amount of the solvent may be used, and is usually from 0.5 to 100 parts by weight, preferably from 1 to 30 parts by weight per 1 part by weight of the adduct salt of 4-(tert-butoxycarbonyl)piperazine compound of formula (3).

The solution of the adduct salt of 4-(tert-butoxycarbonyl) piperazine compound of formula (3) is usually prepared at a temperature that is not higher than the boiling point of the solution and ranges usually from 0 to 120° C., preferably approximately from 20 to 100° C.

The solution containing the adduct salt of 4-(tert-butoxycarbonyl)piperazine compound of formula (3) is typically cooled to precipitate the desired adduct salt at a temperature that is not lower than the freezing point of the solution and ranges usually from −80 to 50° C., preferably approximately from −50 to 30° C.

The solvent that has insufficient solubility with respect to the adduct salt may be selected, for example, from a solvent having a lower polarity such as aliphatic or aromatic hydrocarbon showing insufficient solubility to the crystals to be purified at a precipitating temperature depending on the crystals. The amount thereof is not particularly limited and is usually from 0.5 to 100 parts by weight, preferably from 1 to 30 parts by weight per 1 part by weight of the optically active adduct salt of 4-(tert-butoxycarbonyl)piperazine compound of formula (3).

After the recrystallization, the precipitated adduct salt of optically active 4-(tert-butoxycarbonyl)piperazine compound of formula (3) can be isolated readily by a conventional method, for example, by filtration.

Such recrystallization may be repeated twice or more, if desired.

The adduct salt of the optically active 4-(tert-butoxycarbonyl)piperazine compound of formula (3) can be converted readily into the optically active 4-(tert-butoxycarbonyl)piperazine compound of formula (1') by reacting the compound of formula (3) with a base.

Examples of the base include, for example, an inorganic base such as an alkali metal hydroxide (e.g. sodium hydroxide, potassium hydroxide, or the like), an alkaline earth metal hydroxide (e.g. barium hydroxide, calcium hydroxide, or the like), an alkali metal carbonate (e.g. sodium carbonate, potassium carbonate, or the like), an alkali metal hydrogencarbonate (e.g. sodium hydrogencarbonate, potassium hydrogencarbonate or the like), and an organic base such as diethylamine, triethylamine or the like.

The base is preferably used in an amount of from 0.5 to 30 moles, preferably approximately from 1 to 5 moles per mol of the optically active adduct salt of the optically active 4-(tert-butoxycarbonyl)piperazine compound of formula (3).

The reaction is usually performed in a solvent. Examples of the solvent include, for example, the same solvent that may be used in the reaction of the optically active acid and 4-(tert-butoxycarbonyl)piperazine compound of formula (3). The solvent may be used in an amount of from 0.5 to 100 parts by weight, preferably from 1 to 30 parts by weight per 1 part by weight of the adduct salt of 4-(tert-butoxycarbonyl) piperazine compound of formula (3).

The reaction can be carried out by mixing the adduct salt of the optically active 4-(tert-butoxycarbonyl)piperazine compound of formula (3) and a base; followed by phase separation using water and the water immiscible organic solvent, thereby removing the optically active acid and the base that may be present in the organic layer.

The reaction is usually conducted at a temperature range of from −50 to 100° C., preferably approximately from 0 to 50° C.

After completion of the reaction, the obtained optically active 4-(tert-butoxycarbonyl)piperazine compound of formula (1') can be used in a solution form as it is for the subsequent reaction. The product may also be isolated by distillation of the solvent, or may be isolated by crystallization under cooling in a solvent, followed by filtration to collect the precipitated crystallized product.

Removal of the tert-butoxycarbonyl group of the obtained optically active 4-(tert-butoxycarbonyl)piperazine compound of formula (1') can be accomplished readily by allowing the compound to react with an acid to produce the optically active 1-[(substituted phenyl)phenylmethyl] piperazine of formula (7) or the adduct salt of optically active 1-[(substituted phenyl)phenylmethyl]piperazine of formula (6).

Examples of the acid include, for example, an inorganic acid such as hydrogen chloride, hydrogen bromide, sulfuric acid, or the like, and an organic acid such as methansulfonic acid, trifluoroacetic acid, acetic acid, formic acid or the like.

Any amount of the acid may be used, for example, a catalytic amount of the acid may be used, and the amount is preferably from 0.1 to 50 moles, preferably from 1 to 30 moles per mol of the optically active 4-(tert-butoxycarbonyl) piperazine compound of formula (1).

Examples of the solvent that may be used include, for example, the same solvent as used for the reaction of the optically acid (2) and 4-(tert-butoxycarbonyl)piperazine compound. Any amount of the solvent may be used and it is preferably used in an amount from 0.5 to 100 parts by weight, preferably from 1 to 30 parts by weight per 1 part by weight of the optically active 4-(tert-butoxycarbonyl) piperazine compound of formula (1').

The reaction is preferably performed by mixing an optically active 4-(tert-butoxycarbonyl)piperazine compound of formula (1) and an add in the solvent.

The reaction temperature ranges usually from −20 to 100° C., preferably from 0 to 80° C.

A precipitated adduct salt of the optically active 4-(tert-butoxycarbonyl)piperazine compound of formula (6) can be isolated after completion of the reaction, for example, by collecting the precipitated crystals by filtration.

The optically active 1- [(substituted phenyl) phenylmethyl]piperazine of formula (7) can be produced by adding a base, for example, in a form of an aqueous base solution, followed extraction with water immiscible organic solvent, phase separation, thereby removing the acid that may be present, and then removing the solvent by distillation. The product may be crystallized or precipitated by cooling the organic solvent solution, and the precipitated crystals can be collected by filtration.

EXAMPLE

Hereinafter, the present invention will be described in more detail with reference to Examples, but the present invention is not limited to the Examples.

Example 1

100.0 g (348.7 mmol) of racemic 1-[(4-chlorophenyl) phenylmethyl]piperazine, 1000 g of toluene, 98.9 g (453.3 mmol) of di-tert-butyl dicarboxylate and 200 g of water were added and the temperature was raised up to 35° C. 67.2 g (453.3 mmol) of a 27% aqueous sodium hydroxide solution was added dropwise over 2 hours and then stirring was conducted at that temperature for 3 hours. After separating the water layer of the obtained reaction mixture, 200 g of water was added and washing was conducted, followed by separation of the water layer. After removal of 838 g of the solvent by distillation, 877 g of n-heptane was added and heated up to 64° C., followed by cooling to 0° C. over 6.5 hours. After keeping at that temperature for 2 hours, the crystals formed were collected by filtration and were washed with 270 g of cooled n-heptane/toluene (10/1 (w/w)). The crystals obtained were dried under reduced pressure to yield 118.6 g (306.6 mmol, yield 87.9%) of racemic 1-[(4-chlorophenyl)phenylmethyl]-4-(tert-butoxycarbonyl) piperazine.

Melting point: 136.5–137.2° C. $^1$HNMR (CDCl$_3$) δ 7.38–7.23 (m, 9H), 4.20 (s, 1H), 3.43–3.40 (m, 4H), 2.33–2.30 (m, 4H), 1.43 (s, 9H)

Example 2

To a solution prepared by dissolving 40.0 g (103.4 mmol) of 1-[(4-chlorophenyl)phenylmethyl]-4-(tert-butoxycarbonyl)piperazine in 400 g of toluene, a solution composed of 37.0 g (103.4 mmol) of D-(+)-O,O'-dibenzoyltartaric acid and 25 g of methanol was added at 30° C. After addition of 0.02 g of (−)-1-[(4-chorophenyl) phenylmethyl]-4-(tert-butoxycarbonyl)piperazine-2D-(+)-O,O'-dibenzoyltartaric acid salt as a seed crystal, 400 g of toluene was added dropwise at that temperature over 2 hours. After stirring at the same temperature for 1 hour, the mixture was cooled to 0° C. over 3 hours. After maintain it at this temperature for 2 hours, the crystals formed were collected by filtration and were washed with 80 g of toluene.

The crystals obtained were dried under reduced pressure to yield 40.5 g (36.7 mmol, yield 35.5%) of (−)-1-[(4-chlorophenyl)phenylmethyl]-4-(tert-butoxycarbonyl)piperazine-2D-(+)-O,O'-dibenzoyltartaric acid salt. The optical purity of the (−)-1-[(4-chlorophenyl)phenylmethyl]-4-(tert-butoxycarbonyl)piperazine in the crystals was 70.9% ee.

Example 3

To a solution prepared by dissolving 1.50 g (3.88 mmol) of 1-[(4-chlorophenyl)phenylmethyl]-4-(tert-butoxycarbonyl)piperazine in 15.0 g of toluene, a solution composed of 1.39 g (3.88 mmol) of D-(+)-O,O'-dibenzoyltartaric acid and 0.9 g of methanol was added at 30° C. After addition of (−)-1-[(4-chlorophenyl)phenylmethyl]-4-(tert-butoxycarbonyl)piperazine-2D-(+)-O,O'-dibenzoyltartaric acid salt as a seed crystal, 1.50 g of toluene was added dropwise at that temperature over 0.5 hour, After cooled to 0° C. over 3 hours, the crystals formed were collected by filtration and were washed with toluene. The crystals obtained were dried under reduced pressure to yield 1.34 g (12.1 mmol, yield 31.3%) of (−)-1-[(4-chlorophenyl)phenylmethyl]-4-(tert-butoxycarbonyl)piperazine-2D-(+)-O,O'-dibenzoyltartaric acid salt. The optical purity of the (−)-1-[(4-chlorophenyl)phenylmethyl]-4-(tert-butoxycarbonyl)piperazine in the crystals was 78.1% ee.

Example 4

40.0 g (36.2 mmol, optical purity 70.9% ee) of (−)-1-[(4-chlorophenyl)phenylmethyl]-4-(tert-butoxycarbonyl)piperazine-2D-(+)-O,O'-dibenzoyltartaric acid salt was added to 120 g of acetonitrile and was heated up to 50° C. to dissolve. After cooling of the solution to 45° C. and addition of (−)-1-[(4-chlorophenyl)phenylmethyl]4-(tert-butoxycarbonyl)piperazine-2D-(+)-O,O'-dibenzoyltartaric acid salt as a seed crystal, the mixture was stirred at this temperature for 1 hour and subsequently was cooled to 0° C. over 8 hours. The crystals formed were collected by filtration and were washed with toluene/acetonitrile: 5/1 (v/v). The crystals obtained were dried under reduced pressure to yield 33.7 g (30.5 mmol, yield 84.3%) of (−)-1[-(4-chlorophenyl)phenylmethyl]-4-(tert-butoxycarbonyl)piperazine and 2D-(+)-O,O'-dibenzoyltartaric acid salt. The optical purity of the (−)-1-[(4-chlorophenyl)phenylmethyl]-4-(tert-butoxycarbonyl)piperazine in the crystals was 91.0% ee.

Example 5

2.04 g (1.85 mmol, optical purity 90.6% ee) of (−)-1-[(4-chlorophenyl)phenylmethyl]-4-(tert-butoxycarbonyl)piperazine-2D-(+)-O,O'-dibenzoyltartaric acid salt was added to 6.12 g of acetonitrile and was heated up to 50° C. to dissolve. After cooling of the solution to 45° C. and addition of (−)-1-[(4-chlorophenyl)phenylmethyl]-4-(tert-butoxycarbonyl)piperazine-2D-(+)-O,O'-dibenzoyltartaric acid salt as a seed crystal, the mixture was stirred at this temperature for 1 hour and subsequently was cooled to 0° C. over 8 hours. The crystals formed were collected by filtration and were washed with toluene/acetonitrile: 5/1 (v/v). The crystals obtained were dried under reduced pressure to yield 1.79 g of an acid salt of (1.62 mmol, yield 87.8%) of (−)-1-[(4-chlorophenyl)phenylmethyl]-4-(tert-butoxycarbonyl)piperazine and 2D-(+)-O,O'-dibenzoyltartaric acid. The optical purity of the (−)-1-[(4-chlorophenyl)phenylmethyl]-4-(tert-butoxycarbonyl)piperazine in the crystals was 98.2% ee.

Melting point: 136.3–137.6° C.

Example 6

1.50 g (1.36 mmol, optical purity 98.2% ee) of (−)-1-[(4-chlorophenyl)phenylmethyl]-4-(tert-butoxycarbonyl)piperazine-2D-(+)-O,O'-dibenzoyltartaric acid salt was suspended in 15 g of toluene. 7.8 g (5.44 mmol) of a 2.8% aqueous sodium hydroxide solution was added at 20° C. and stirred at this temperature for 30 minutes. After separating the water layer of the reaction mixture obtained, 7.8 g (1.95 mmol) of a 1% aqueous sodium hydroxide solution was further added at that temperature and stirred for 30 minutes. After separation of the water layer, 7.8 g of water was added to wash and the water layer was separated. The solvent of the separated organic layer was distilled to yield 0.474 g (1.22 mmol, yield 90.0%) of (−)-1-[(4-chlorophenyl)phenylmethyl]-4-(tert-butoxycarbonyl)piperazine as crystals. The optical purity was 98.4% ee.

Melting point: 157.1–158.5° C. Angle of rotation: $[\alpha]_D$−7.0° (c=0.2, toluene)

Example 7

To a solution prepared by introducing 7.38 g (202.4 mmol) of hydrogen chloride gas in 43.5 g of ethyl acetate, a solution of 7.83 g (20.24 mmol, optical purity 99.6% ee) of (−)-1-[(4-chlorophenyl)phenylmethyl]-4-(tert-butoxycarbonyl)piperazine in 146.6 g of toluene was added dropwise at 20° C. over 1 hour. After stirring at that temperature, the mixture was heated up to 60° C. for 30 minutes and was stirred at this temperature for 3 hours. After cooling to 20° C., the crystals formed were collected by filtration and were washed with toluene. The crystals obtained were dried under reduced pressure to yield 7.29 g (20.27 mmol, the yield was quantitative) of (−)-1-[(4-chlorophenyl)phenylmethyl]piperazine dihydrochloride. The optical purity of the (−)-1-[(4-chlorophenyl)phenylmethyl]piperazine in the crystals was 99.5% ee.

Example 8

To a solution of 0.19 g (0.49 mmol, optical purity 64.8% ee) of (−)-1-[(4-chlorophenyl)phenylmethyl]-4-(tert-butoxycarbonyl)piperazine in 10.0 g of toluene, 7.0 g of water, 35% hydrochloric acid and 1.0 g of methanol were added. The mixture was heated up to 60° C. and was stirred for 5 hours. After separation of the organic layer of the reaction mixture, 10.0 g of toluene was added to the water layer and 2.15 g of a 27% aqueous sodium hydroxide solution was added to adjust pH of the mixed solution to 12 or more. After separating a water layer, water was added to the oil layer to wash and the water layer was separated. The solvent of the oil layer obtained was removed by distillation to yield 0.14 g (0.49 mmol, the yield was quantitative) of (−)-1-[(4-chlorophenyl)phenylmethyl]piperazine as crystals. The optical purity was 67.4% ee.

Example 9

To a solution prepared by dissolving 40.0 g (103.4 mmol) of 1-[(4-chlorophenyl)phenylmethyl]-4-(tert-butoxycarbonyl)piperazine in 400 g of toluene, a solution of 38.9 g (103.4 mmol) of L-(−)-O,O'-dibenzoyltartaric acid monohydrate in 23 g of methanol was added at 20° C. After addition of 0.02 g of (+)-1-[(4-chlorophenyl)phenylmethyl]-

4-(tert-butoxycarbonyl)piperazine-2L-(−)-O,O'-dibenzoyltartaric add salt as a seed crystal, 400 g of toluene was added dropwise at that temperature over 2 hours. After stirring at the same temperature for 1 hour, the mixture was cooled to 0° C. over 5 hours and maintained at this temperature for 2 hours. The crystals formed were collected by filtration and were washed with 80 g of toluene to yield 66.6 g of crystals containing (+)-1-[(4-chlorophenyl)phenylmethyl]-4-(tert-butoxycarbonyl)piperazine-2L-(−)-O,O'-dibenzoyltartaric acid salt and the solvent. The optical purity of the (+)-1-[(4-chlorophenyl)phenylmethyl]-4-(tert-butoxycarbonyl)piperazine in the crystals was 70.9% ee. The crystals obtained were used for subsequent recrystallization without being dried.

60.0 g (optical purity 70.9% ee) of the crystals containing (+)-1-[(4-chlorophenyl)phenylmethyl]-4-(tert-butoxycarbonyl)piperazine-2L-(−)-O,O'-dibenzoyltartaric acid salt and the solvent was added to 111 g of acetonitrile, and was heated up to 55° C. to dissolve. After cooling of the solution to 45° C. and addition of (+)-1-[(4-chlorophenyl)phenylmethyl]-4-(tert-butoxycarbony1)piperazine2L-(−)-O,O'-dibenzoyltartaric acid salt as a seed crystal, the mixture was stirred at this temperature for 1 hour and subsequently was cooled to 0° C. over 8 hours. The crystals formed were collected by filtration and were washed with toluene/acetonitrile: 5/1 (v/v) to yield 56.8 g of 2L-(−)-O,O'-dibenzoyltartaric acid salt of (+)-1-[(4-chlorophenyl)phenylmethyl]-4-(tert-butoxycarbonyl)piperazine. The optical purity of the (+)-1-[(4-chlorophenyl)phenylmethyl]-4-(tert-butoxycarbonyl)piperazine in the crystals was 93.0% ee. The crystals obtained were used for subsequent recrystallization without being separated.

54.6 g (optical purity 93.0% ee) of the crystals containing (+)-1-[(4-chlorophenyl)phenylmethyl]-4-(tert-butoxycarbonyl)piperazine-2L-(−)-O,O'-dibenzoyltartaric acid salt and the solvent was added to 111 g of acetonitrile, and was heated up to 60° C. to dissolve. After cooling of the solution to 50° C. and addition of (+)-1-[(4-chlorophenyl)phenylmethyl]-4-(tert-butoxycarbonyl)piperazine-2L-(−)-O,O'-dibenzoyltartaric acid salt as a seed crystal, the resulting mixture was stirred at this temperature for 1 hour and subsequently was cooled to 0° C. over 8 hours. The crystals formed were collected by filtration and were washed with toluene/acetonitrile:5/1 (v/v). The crystals were dried under reduced pressure to yield 31.0 g (28.1 mmol) of (+)-1-[(4-chlorophenyl)phenylmethyl]-4-(tert-butoxycarbonyl)piperazine-2L-(−)-O,O'-dibenzoyltartaric acid salt (the yield from the racemic 1-[(4-chlorophenyl)phenylmethyl]-4-(tert-butoxycarbonyl)piperazine was 31.3%). The optical purity of the (+)-1-[(4-chlorophenyl)phenylnethyl]-4-(tert-butoxycarbony1)piperazine in the crystals was 98.3% ee.

Melting point: 134.6–135.7° C.

Example 10

30.0 g (27.2 mmol, optical purity 98.3% ee) of (+)-1-[(4-chlorophenyl)phenylmethyl]-4-(tert-butoxycarbonyl)piperazine-2D-(−)-O,O'-dibenzoyltartaric acid salt was suspended in 150 g of toluene. 155.4 g (108.8 mmol) of a 2.8% aqueous sodium hydroxide solution was added at 20° C. and stirred at this temperature for 30 minutes. After separating the water layer of the reaction mixture, 155.4 g (38.9 mmol) of a 1% aqueous sodium hydroxide solution was further added at that temperature and stirred for 30 minutes. After separation of the water layer, 155.4 g of water was added to wash and the separated water layer was removed to yield 178.2 g of a solution containing (+)-1-[(4-chlorophenyl)phenylmethyl]-4-(tert-butoxycarbonyl)piperazine. The optical purity was 98.0% ee. The solution obtained was used directly for the subsequent reaction. (Aportion of the solvent was removed from the solution. As for the obtained (+)-1-[(4-chlorophenyl)phenylmethyl]-4-(tert-butoxycarbony)piperazine, the following data of physical properties were obtained.)

Melting point: 155.5–156.3° C.

Angle of rotation: $[\alpha]_D$ +7.5° (c=0.2, toluene)

To a solution prepared by introducing 7.78 g (213.3 mmol) of hydrogen chloride gas in 45.9 g of ethyl acetate, 176.0 g of a solution containing the obtained (+)-1-[(4-chlorophenyl)phenylmethyl]-4-(tert-butoxycarbonyl)piperazine (optical purity 98.0% ee) was added dropwise at 20° C. over 1 hour. After stirring at that temperature, the mixture was heated up to 60° C. for 30 minutes and was stirred at this temperature for 3 hours. After cooling to 20° C., the crystals formed were collected by filtration and were washed with toluene. The crystals obtained were dried under reduced pressure to yield 8.51 g (23.7 mmol) of (+)-1-[(4-chlorophenyl)phenylmethyl]piperazine dihydrochloride from the (+)-1-[(4-chlorophenyl)phenylmethyl]-4-(tert-butoxycarbonyl)piperazine-2D-(−)-O,O'-dibenzoyltartaric acid salt in a yield of 88.1%. The optical purity of the (+)-1-[(4-chlorophenyl)phenylmethyl]piperazine in the crystals was 98.4% ee.

What is claimed is:

1. An optically active 4-(tert-butoxycarbonyl)piperazine compound of formula (1'):

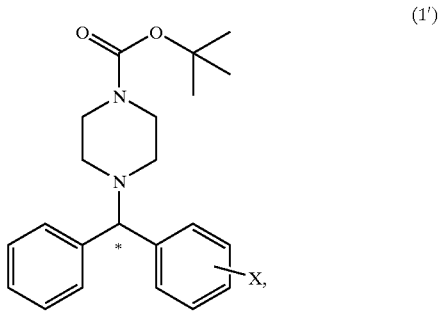

wherein X denotes a chlorine atom, a C1–C3 alkyl group or a C1–C3 alkoxy group and * designates an asymmetric carbon atom.

2. A composition comprising an optical isomer of formula

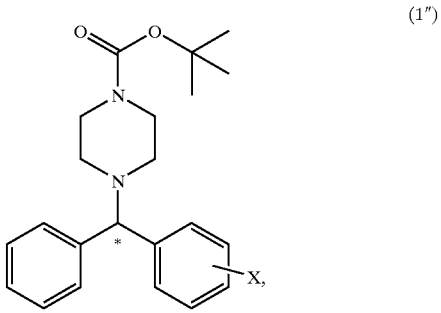

wherein X denotes a chlorine atom, a C1–C3 alkyl group or a C1–C3 alkoxy group and * designates an asymmetric carbon atom, and an enantiomer thereof, wherein one optical isomer is present in excess to the enantiomer thereof.

3. A 4-(tert-butoxycarbonyl)piperazine compound of formula (1):

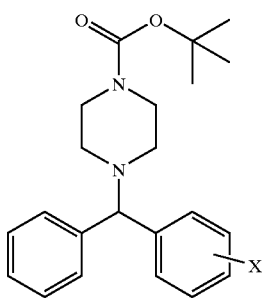

wherein X denotes a chlorine atom, a C1–C3 alkyl group or a C1–C3 alkoxy group.

4. An optical isomer of formula (1"):

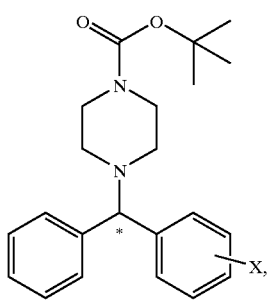

wherein X denotes a chlorine atom, a C1–C3 alkyl group or a C1–C3 alkoxy group and * designates an asymmetric carbon atom, or salts thereof.

5. An adduct salt of formula (3):

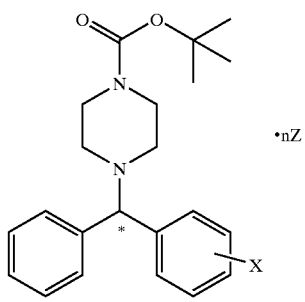

wherein X denotes a chlorine atom, a C1–C3 alkyl group or a C1–C3 alkoxy group and * designates an asymmetric carbon atom, n represents en integer of 1 or 2, and Z represents an optically active acid of formula (2):

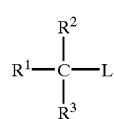

wherein L represents —COOH or —SO$_3$H,

R$^2$ represents a hydrogen atom or a hydroxyl group,

R$^1$ and R$^3$ are the same or different and each independently represent a hydrogen atom, a halogen atom, an arylcarbonyloxy group, a linear or branched alkyl group which may be substituted with at least one group selected from the group consisting of a hydroxyl group, a halogen atom, an arylcarbonyloxy group, a carboxy group and an arylaminocarbonyl group;

an aryl group which may be substituted with at least one group selected from the group consisting of a halogen atom, an alkyl group and an alkoxy group;

an aralkyl group which may be substituted with at least one group selected from the group consisting of a halogen atom, an alkyl group, an alkoxy group and a hydroxyl group;

an aryloxy group which may be substituted with at least one group selected from the group consisting of a halogen atom, an alkyl group, an alkoxy group and a hydroxyl group;

a cyclic alkyloxy group which may be substituted with at least one group selected from the group consisting of a halogen atom, an alkyl group, an alkoxy group and a hydroxyl group; or a cyclic alkyl group which may be substituted with at least one group selected from the group consisting of a halogen atom, an alkyl group, an alkoxy group, a hydroxyl group and a phenylcarbonylamino group; or R$^1$ and R$^3$ may be bonded together to form an alkylene group which may be substituted with at least one group selected from the group consisting of a halogen atom, an alkyl group, an alkoxy group, a carboxyl group, an oxo group, a hydroxyl group, and a phenylcarbonylamino group, or a heterocycle which may be substituted with at least one group selected from the group consisting of an alkyl group, alkoxy or a halogen atom.

6. An adduct salt according to claim 5, wherein the acid of formula (2) is optically active O,O'-dibenzoyltartaric acid.

7. An adduct salt according to any one of claim 5 or 6 wherein X represents a chlorine atom at 4-position of the phenyl group.

8. A process for producing a 4-(tert-butoxycarbonyl) piperazine compound of formula (1):

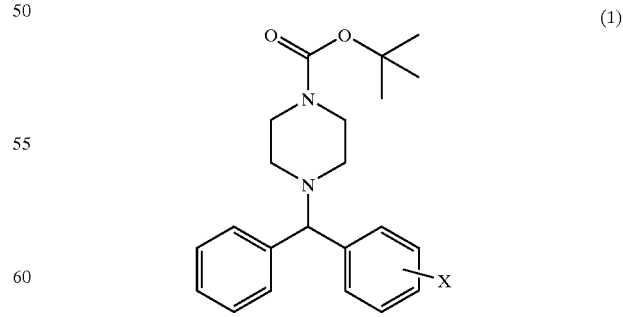

wherein X denotes a chlorine atom, a C1–C3 alkyl group or a C1–C3 alkoxy group, which comprises reacting 1-[(substituted phenyl) phenylmethyl]piperazine of formula (4):

(4)

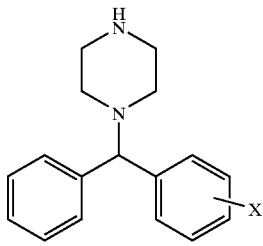

wherein X has the same meaning as defined above, with di-tert-butyl dicarbonate of formula (5):

[(CH₃)₃COCO]₂O(5).

9. A process for producing an optically active adduct salt of formula (3):

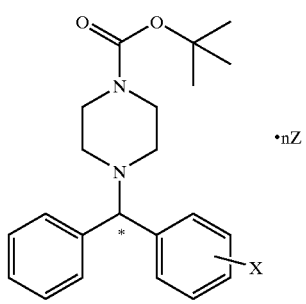

(3)

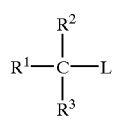

wherein X denotes a chlorine atom, a C1–C3 alkyl group or a C1–C3 alkoxy group, * represents an asymmetric carbon atom, and n represents an integer of 1 or 2, and Z represents an optically active acid of formula (2):

$$R^1—\underset{R^3}{\underset{|}{\overset{R^2}{\overset{|}{C}}}}—L \quad (2)$$

wherein L represents —COOH or —SO₃H,

R² represents a hydrogen atom or a hydroxyl group;

R¹ and R³ are the same or different and independently represent a hydrogen atom, a halogen atom, or an arylcarbonyloxy group;

a linear or branched alkyl group which may be substituted with at least one group selected from the group consisting of a hydroxyl group, a halogen atom, an arylcarbonyloxy group, a carboxy group and an arylaminocarbonyl group;

an aryl group which may be substituted with at least one group selected from the group consisting of a halogen atom, an alkyl group and an alkoxy group;

an aralkyl group which may be substituted with at least one group selected from the group consisting of a halogen atom, an alkyl group, an alkoxy group and a hydroxyl group;

an aryloxy group which may be substituted with at least one group selected from the group consisting of a halogen atom, an alkyl group, an alkoxy group and a hydroxyl group;

a cyclic alkyloxy group which may be substituted with at least one group selected from the group consisting of a halogen atom, an alkyl group, an alkoxy group and a hydroxyl group; or a cyclic alkyl group which may be substituted with at least one group selected from the group consisting of a halogen atom, an alkyl group, an alkoxy group a hydroxyl group and a phenylcarbonylamino group; or R¹ and R³ may be bonded together to form an alkylene group which may be substituted with at least one group selected from the group consisting of a halogen atom, an alkyl group, an alkoxy group, a carboxyl group, an oxo group, a hydroxyl group, and a phenylcarbonylamino group, or a heterocycle which may be substituted with at least one group selected from the group consisting of an alkyl group, an alkoxy group and a halogen atom, which comprises reacting a composition comprising an optical isomer of 4-(tert-butoxycarbonyl)piperazine compound of formula (1"):

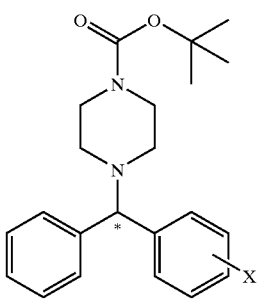

(1")

wherein X and * are as defined above, and an enantiomer thereof, with an optically active acid of formula (2) as defined above and isolating the resulting adduct salt.

10. A process according to claim 9, which further comprises recrystallizing the acid adduct salt of the optically active 4-(tert-butoxycarbonyl)piperazine of formula (3).

11. A process according to claim 9 or 10, which further comprises reacting an adduct salt of formula (3), with a base to produce an optically active 4-(tert-butoxycarbonyl)piperazine of formula (1'):

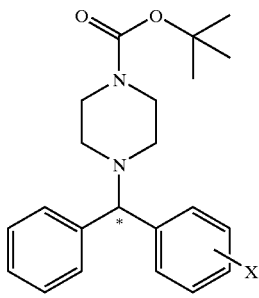

(1')

wherein X denotes a chlorine atom, a C1–C3 alkyl group or a C1–C3 alkoxy group and * designates an asymmetric carbon atom.

12. A process for producing an optically active adduct salt of formula (6):

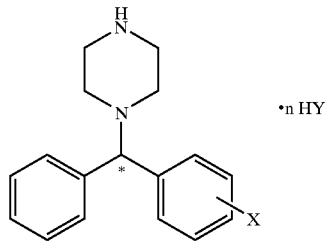

(6)

wherein X denotes a chlorine atom, a C1–C3 alkyl group or a C1–C3 alkoxy group, * represents an asymmetric carbon atom, and n represents an integer of 1 or 2, Y represents a halogen atom, —OSO₃H, —OSO₂CH₃, —OCOCF₃, —OCOCH₃ and —OCOH which comprises reacting an optically active 4-(tert-butoxycarbonyl)piperazine of formula (1'):

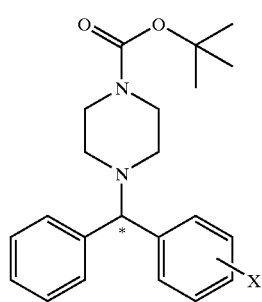

(1')

wherein X and * are as defined above with an acid of formula: HY, wherein Y represents the same as defined above.

13. A process for producing an optically active 1-[substituted phenyl)phenylmethyl]piperazine of formula (7):

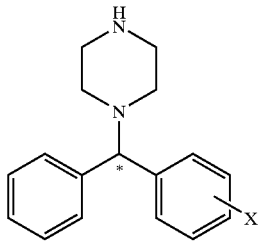

(7)

wherein X denotes a chlorine atom, a C1–C3 alkyl group or a C1–C3 alkoxy group, and * represents an asymmetric carbon atom, which process comprises reacting an optically active 4-(tert-butoxycarbonyl)piperazine compound of formula (1'):

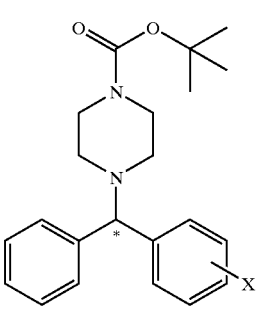

(1')

wherein X denotes a chlorine atom, a C1–C3 alkyl group or a C1–C3 alkoxy group, and * represents an asymmetric carbon atom, with an acid and subsequently with a base.

14. A compound as in claim 1, wherein X represents a chlorine atom at 4-position of the phenyl group.

15. A compound as in claim 2, wherein X represents a chlorine atom at 4-position of the phenyl group.

16. A compound as in claim 3, wherein X represents a chlorine atom at 4-position of the phenyl group.

17. An optical isomer as in claim 4, wherein X represents a chlorine atoms at 4-position of the phenyl group.

* * * * *